United States Patent [19]

McCloskey

[11] 4,035,239

[45] July 12, 1977

[54] ENZYMIC ASSAY FOR ACETATE ION

[76] Inventor: Leo P. McCloskey, 339 Stanford Ave., Santa Cruz, Calif. 95062

[21] Appl. No.: 684,791

[22] Filed: May 10, 1976

[51] Int. Cl.² .................. G01N 31/14; G01N 33/00
[52] U.S. Cl. .......................... 195/103.5 R; 195/99
[58] Field of Search ....................... 195/103.5 R, 99

[56] References Cited

PUBLICATIONS

Kuo et al. "A Specific Micromethod for Determination of Acetyl Residues in Proteins" Analytical Biochem. 55, 1-8 (1973).

Bergmeyer et al. "Method of Enzymatic Analysis" Verlag Chemie Weinheim, AP, Inc. N.Y., San Francisco, London (1974) pp. 1520–1528.

Primary Examiner—Alvin E. Tanenholtz
Assistant Examiner—C. A. Fan
Attorney, Agent, or Firm—Flehr, Hohbach, Test, Albritton & Herbert

[57] ABSTRACT

An improved enzymic assay and assay composition for acetate ion in a biological fluid (e.g., blood serum or tissue extract) or a solution of fruit juice origin (e.g., wine). The acetate ion is reacted with adenosine triphosphate in the presence of enzymic quantities of phosphotransacetylase to form adenosine diphosphate. The above procedure is accelerated by the presence of Coenzyme A and phosphotransacetylase enzyme during the formation of adenosine diphosphate. Thereafter, the quantity of adenosine diphosphate may be assayed by known enzymic techniques. The procedure may be employed for analysis of acetate esters (e.g., ethyl acetate) by hydrolysis to acetate ion in the presence of esterase.

8 Claims, No Drawings

ENZYMIC ASSAY FOR ACETATE ION

BACKGROUND OF THE INVENTION

The present invention relates to the enzymic assay for acetate ion in a liquid sample, particularly liquids of fruits juice or biological origin.

It is important to analyze for acetate ion in solutions of fruit juice origin such as wine. The acetic acid level in wine is important to the enologist and the wine maker as an indicator of quality control or spoilage. In one detection technique, the acetate ion is reacted with adenosine triphosphate (ATP) in the presence of acetate kinase (AK) to form acetyl-phosphate and adenosine diphosphate (ADP). Then the acetyl-phosphate is used as the basis for analysis in a colorimetric assay by wet chemistry. This assay technique suffers from the disadvantages of being slow, relatively inaccurate and only being adaptable to the assay of white wine.

Acetate esters such as ethyl acetate provide an objectionable taste to the consumer of wines. Therefore, a simple, efficient assay for such esters would be advantageous.

In clinical biochemistry, the determination of the acetate ion is important, especially in the areas of research involving kidney dialysis. However, known techniques are not subject to rapid and repeatable results with relatively inexpensive equipment.

A technique has been described for the determination of acetyl residues in protein as set forth in an article by Kuo et al entitled "A specific Micromethod for Determination of Acetyl Residues in Proteins", *Analytical Biochemistry*, 55, 1–8 (1973). This paper describes cleavage of the acetyl group from the protein under pressure in a wet chemical hydrolysis reaction. This acetate ion is then reacted with ATP in the presence of AK to form acetyl phosphate and ADP. The ADP is reacted with phosphoenolpyruvate (PEP) in the presence of pyruvate kinase (PK) to form ATP + pyruvate. The latter compound is then reacted with reduced nicotinamide adenine dinucleotide (NADH) in the presence of lactate dehydrogenase (LDH) enzyme. The amount of reduced NADH (colored) converted to oxidized nicotinamide adenine dinucleotide (NAD$^+$) (uncolored) is detected optically to determine the quantity of acetate ion present in the product of hydrolysis. There is no disclosure that the above procedure could be employed for the detection of acetate ion present as such in a biological fluid such as serum or in a fluid such as wine or other fruit juice based products.

The technique disclosed in the Kuo et al. paper is subject to a number of significant disadvantages. One is that the reaction to form acetyl phosphate and ADP is relatively slow resulting in a total time on the order of 60 to 90 minutes. This is an obvious economic disadvantage when a large number of samples are to be analyzed by a technician. Furthermore, since the enzymic reactants are not totally stable, relatively long reaction times can be accompanied by deterioration to cause a lack of repeatability of the analytical results.

SUMMARY OF THE INVENTION AND OBJECTS

In accordance with the present invention, an improved enzymic assay and assay composition are provided for acetate ion in a sample fluid, particularly of biological or fruit juice origin. In one embodiment relevant to the latter type of fluid, particularly wine, the acetate ion is reacted with adenosine triphosphate (ATP) in the presence of acetate kinase (AK) to yield acetyl-phosphate and adenosine disphosphate (ADP). The latter compound is quantitated by any conventional technique measuring one of the reaction products. In a preferred embodiment, the acetate ion reaction is accelerated by trapping acetyle-phosphate, the rate limiting reaction product, in accordance with the following equation:

Acetate + ATP + CoA $\underset{AK}{\overset{PTA}{\rightleftharpoons}}$ acetyl-CoA + ADP     (1)

For rapid, repeatable results, it has been found that all regents, except for AK, may be premixed and incubated for a sufficient time to produce a stable reading by a detector. This preliminary incubation step minimizes undesirable interference in the reading from contaminants in the reagents. Thereafter, the procedure is commenced by the addition of AK.

The above procedure may be employed for the detection of acetate esters such as ethyl acetate, of particular concern in wine. This is accomplished by hydrolyzing the ester in the presence of esterase to form acetate ion, followed by the procedure outlined above.

It is an object of the invention to provide an improved rapid enzymic assay for the detection of acetate ion.

It is a particular object of the invention to provide such an assay for acetate ion in a biological fluid such as serum or tissue.

It is a further object to provide such an assay for the detection of acetate ion in a fluid of fruit juice origin.

It is another object of the invention to provide an assay for acetate esters such as are present in the fluids of the preceding paragraph.

It is an additional object to provide assay of the foregoing type which is relatively inexpensive, rapid, and repeatable.

It is a particular object of the invention to provide a composition suitable for rapid assay of the foregoing type by technicians with relatively limited instructions.

Further objects and features of the invention will be apparent from the following description in which the preferred embodiments of the invention have been set forth in detail.

DETAILED DESCRIPTION OF THE PREFERRED EMBODIMENTS

The present invention is directed to the assay of acetate ion in fluids of biological or fruit juice origin. This technique is based in part upon the aforementioned Kuo technique for the determination of acetyl residues in protein. In contrast, the present invention is directed to the assay fo acetate ion present as such in the fluids (except for acetate esters). Such fluids include those of biological origin such as serum or tissue extract and those of fruit juice origin such as wine. Such fluids also include samples from the production of organic chemicals and drug. As defined herein, acetate ion refers to the ionized form of the acetate radical.

For convenience of reference, the following standard abbreviations will be employed in the present specification:

HEPES = N-2-hydroxyethlpiperazine-N'-ethanesulfonic acid
AK = acetate kinase

PK = pyruvate kinase
LDH = lactate dehydrogenase
PEP = phosphoenolpyruvate
ATP = adenosine triphosphate
ADP = adenosine diphosphate
NAD+ = oxidized nicotinamide adenine dinucleotide (colorless at 340nm)
NADH = reduced nicotinamide adenine dinucleotide (colored at 340nm)
CoA = Coenzyme A
PTA = phosphotransacetylase assay equation: 4

The reaction which forms the basis of the present assay is set forth in the following equation:

Acetate + ATP $\overset{AK}{=}$ acetyl-phosphate + ADP  (2)

The amount of adenosine diphosphate (ADP) produced in the above reaction is then used as the basis for determining the presence of the acetate ion in the original sample solution by known techniques. One enzymic scheme for assaying the ADP formed in equation (2) is as follows:

ADP + PEP $\overset{PK}{=}$ ATP + pyruvate  (3)
Pyruvate + NADH + H $\overset{LDH}{=}$ lactate + NAD⁺  (4)

The above general scheme is generally described in the Kuo article with respect to the detection of acetyl residues and proteins. The production of pyruvate in Equation (3) is a measure of the ADP formed in Equation (2). Similarly, the amount of oxidation in Equation (4) is an assay of the presence of pyruvate formed in Equation (3). The extent of oxidation is measured by the change in absorbance detected with a spectrophotometer at the optimum wavelength (e.g., 340nm).

There is no suggestion in the Kuo article that the scheme could be employed for the detection of acetate ions naturally present in the sample solution. In particular, there is no suggestion that this technique could be employed to assay acetate ion in a fluid of fruit juice origin. Such as assay is particularly important in the wine industry because the level of acetate ion has a significant affect upon the taste and stability of the wine. Adaption of the Kuo technique to the wine industry has been found to be a significant improvement over presently employed techniques for acetate ion.

One of the disadvantages of the foregoing basic technique (Equations (2) –(4) ) is that the enzymic assay reactions may take on the order of 60 to 90 minutes for completion. This requires significant time and may be a problem in terms of repeatability of the procedure due to the possible instability of enzymic reagents.

It has been found that the rate limiting reaction product important to increase the rate of the foregoing procedure is the acetyl-phosphate. It is strictly an end product as it does not enter subsequent assay reactions. In accordance with the preferred mode of the present invention, the acetyl-phosphate may be efficiently and rapidly "trapped" to yield significantly faster assay reactions. The preferred technique for trapping or removing the acetyl-phosphate is by the following equation:

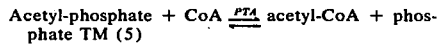
Acetyl-phosphate + CoA $\overset{PTA}{=}$ acetyl-CoA + phosphate TM (5)

To simplify the assay technique for a technician, a premixture of all of the reagents employed in Equations (2)–(5), except one essential reaction component, may be mixed with the sample fluid and the reactions allowed to proceed simultaneously. Since reaction (5) is so rapid, Equations (2)–(5) may be combined for all practical purpose to provide the following overall or net reaction:

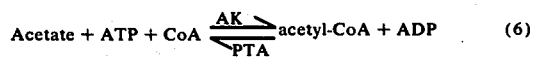
Acetate + ATP + CoA $\overset{AK}{\underset{PTA}{\rightleftharpoons}}$ acetyl-CoA + ADP  (6)

It is preferable to perform an optional preliminary incubation step to avoid inaccuracies in the readings due to possible interfering reactive contaminants in the mixed reagents which would be detected as if it were acetate ion. One mode of performing this preliminary incubation step is by premixing the sample fluid and all of the reagents employed in the foregoing procedure with the exception of acetate kinase (AK). Then the product is incubated for sufficient time to produce an essentially stable reading by a detection of absorbance at 340nm, the maximum adsorption of ultraviolet light of redued nicotinamide adenine dinucleotide (NADH). Stabilization of the reading in the absence of AK takes into account any other sources of oxidation of NADH. A suitable incubation time is on the order of 5 to 15 minutes. It is noted that this step could also be employed in the absence of the sample since the primary purpose is to adjust for contamination in the reagents. However, it is preferably performed in the presence of the sample fluid to also avoid reduction of the NADH by contaminants present in the sample fluid.

A preferable composition for assaying acetate ion in sample fluids of the foregoing type includes the reagents of the foregoing equation (6) with the exception of the AK for the reasons set forth in the preceding paragraph. Such a sample fluid comprises Coenzyme A (CoA), phosphotransacetylase (PTA), and adenosine triphosphate (ATP), together with the other reagents to be employed for subsequent analysis of the ADP reaction product in equation (6). In the technique set forth in equations (3) and (4), such other reagents are pyruvate kinase (PK), lactate dehydrogenase (LDH), phosphoenolpyruvate (PEP), and NADH is apropriate quantites. After incubation, as set forth above, the AK may be added to the assay composition. The overall composition is suitably buffered at a slightly alkaline PH of about 7.4 since the reactions are maximized at such PH levels. For example, HEPES buffer (N-2-hydroxyethylpiperazine-N'-ethanesulfonic acid) may be utilized for this purpose.

The buffer preferbly include magnesium ion to facilitate the reaction of equation (3).

A suitable premixed enzymic composition which includes all necessary reagents for the procedure of equations (2), (3), (4) and (6) with the exception of the AK is as follows:

TABLE 1

| Component | Range | |
|---|---|---|
| HEPES | 0.1–0.2 | molar (M) |
| ATP | 2–5 | mM |
| NADH | 0.1–0.2 | mM |
| magnesium ion | 7.5 | mM |
| potassium ion | 50–60 | mM |
| phosphoenolpyruvate | 1.5–2.0 | mM |
| Coenzyme A | 0.2 | mM |
| Enzymes: | | |
| Pyruvate Kinase | 2 | IU per ml |
| Lactate Dehydrogenase | 2 | IU per ml |
| Phosphotransacetylase | 4 | IU per ml |

A reagent made to these specifications in Table 1 should be incubated for 5–15 minutes or until the absorbance substantially stabilizes. To the above mixture, with sample, the AK may be added at a concentration of approximately 5 milligrams AK per ml. A suitable level of AK is 8.5 IU/ml, identified by the code ED 2.7.2.1 of the Enzyme Commission.

In one technique for carrying out the present assay, a sample fluid containing acetate ion, suitably at 0.5–10 m molar concentration, is first mixed with the ingredients of Table 1. The absorbance, $E_1$, is read at approximately 340 nm after about 2 to 5 minutes of incubation. Thereafter, the assay reactions are commenced by the addition of AK and the total composition is incubated at a temperature of about 20°–30° C. for approximately 10–30 minutes. The final absorbance at th same wavelength is measured as $E_2$. The change in absorbance, $\Delta E$, is calculated by subtracting $E_2$ from $E_1$. A blank sample is made by measuring the level of absorbance of distilled water. The value of $\Delta E$ is then corrected by substracting the $\Delta E$ of the blank found with the distilled water.

Sufficient NADH must be present initially to be in excess of the acetate ion to be assayed together with the amount of NADH which is oxidized by contaminants during the incubation step. For readings by a conventional spectrophotometer, it is preferable that at least 0.8 molar NADH be present during the final reading.

In another embodiment of the invention, acetate esters such as ethyl acetate may also be assayed. It is well known that ethyl acetate has a highly objectionable organoleptic characteristic which is a particular problem when present in wine. The present technique may be employed for this purpose by first hydrolyzing the acetate ester to form the acetate ion and then performing the foregoing procedure. A referred mode of hydrolysis is as follows:

$$\text{Acetate ester} + H_2O \xrightarrow{\text{esterase}} \text{alcohol} + \text{acetic acid} \qquad (7)$$

This hydrolysis technique is preferable because it is rapid and complete. A suitable esterase enzyme is identified by Code EC 3.1.1.1 of the Enzyme Commission.

In carrying out the hydrolysis for the assay of wine, the sample containing the acetate ester is first mixed with esterase in a buffered medium at 22–30° C. A suitable buffered medium is a pH 8.0 HEPES buffer (N-2-hydroxyethylpiperazine-N'-ethanesulfonic acid) at 0.2 molar and 50 IU per ml of the enzyme esterase.

The acetate ion product of hydrolysis may be assayed in accordance with the foregoing procedure of Equations (3), (4) and (6). By performing two assays, one including the hydrolysis step and one without it, the difference when multiplied by an appropriate factor comprises the acetate ester. For example, when it is suspected that ethyl acetate is the predominant acetate ester, as in wine, the difference is multiplied by a factor of 1.45.

It should be understood that the assay technique to analyze for ADP of equations (3) and (4) is only one conventional known technique. However, the present invention encompasses within its scope any other technique for the analysis of ADP.

Conventional techniques may be employed to dilute or decolorize samples which are heavily colored. This may be a factor for the use of relatively inexpensive spectrophotometers. Clinical samples of biological origin such as blood serum or tissue extracts should be deproteinized in a standard manner. Suitable standard techniques of this type are set forth in Bergmeyer, Hans U., *Methods of Enzymatic Analysis*, Vol. 1, AP and Verlag Chemie, New York, New York, 1974.

It should be understood that preparation of the reagents for the present invention may be modified to facilitate analysis of specific samples. In addition, such reagents may be packaged for in-lab use. For this purpose, it may be desirable to employ stabilizers to extend the shelf-life of the reagent compositions. In addition, such compositions may be employed in lyophilized form. Conventional stabilizers for enzymes include bovine serum albumin. Also, mannitol may be employed to stablize tha NADH. Furthermore, bulking agents may be added to facilitate the solution of lyophilized preparations.

A further disclosure of the nature of the present invention is provided by the following specific examples of the practice of the invention. It should be understood that the data disclosed serve only as examples and are not intended to limit the scope of the invention.

EXAMPLE 1

A technique for performing the present invention using the procedures of the foregoing equations (3), (4) and (6) is as follows.

Reagent A is made of the concentrations of the components listed below to a pH of 7.4.

| Component | Range |
|---|---|
| HEPES | 0.1 molar (M) |
| ATP | 5 mM |
| NADH | 0.2 mM |
| magnesium ion | 7.5 mM |
| potassium ion | 60 mM |
| phosphoenolpyruvate | 2.0 mM |
| Coenzyme A | 0.2 mM |
| Enzymes: | |
| Pyruvate Kinase | 2 IU per ml |
| Lactate Dehydrogenase | 2 IU per ml |
| Phosphotransacetylase | 4 IU per ml |

Reagent B is filled with acetate kinase enzyme at approximately 5 mg/ml at 8.5 IU/ml.

A sample fluid of wine with an acetate ion level of 0.5–10 m molar at a volume of 25 ul is added to the composition kof Reagent A to form a total volume of 3.025 ml. The mixture is incubated for about 5 minutes. Thereafter, the absorbance, $E_1$, is recorded on a spectrophotometer at 340 nm with a light path of 1 cm. Sample may also be added to Reagent A in volumes larger than 25 ul, up to 500 ul, with appropriate dilution of sample into the 0.5–10 millimotor range of acetate ion.

Thereafter, 10 $\mu$ of vial B is added to the above mixture which is incubated at 20°–30° C for 10 to 30 minutes. The final absorbance, $E_2$, is recorded. $\Delta E$ is calculated by subtracting the $E_2$, is recorded. $\Delta E$ is calculated by subtracting the $E_2$ value from the $E_1$ value.

A blank is made by the substitution of an equal to sample volume of distilled water instead of the sample in the foregoing analysis. This value $\Delta E_{blank}$, is subtracted from the $\Delta E$ to adjust for interference from contaminants in the water or acetate kinase, Reagent B. This corrected $\Delta E$ is then compared with a standard curve to determine actual acetate ion concentration

EXAMPLE 2

The foregoing procedure is employed to determine the acetate ester concentration. A vial C is employed in addition to vials A and B of Example B 1. Vial C includes the hydrolysis reagents for the acetate ester in a buffered medium. This mixture comprises 0.2 m HEPES buffered at a pH 8.0, and 50 IU per ml of enzyme esterase class EC 3.1.1.1. 25 µl of the wine are mixed with 500 µl of vial C. The contents are incubated for about 30–70 minutes at 22 to 30° C. Then this fluid is assayed for acetate ion with vials A and B of Example 1. A blank is run with distilled water to correct the ΔE for contaminants in both the esterase and acetate kinase. The acetate measured in accordance with the foregoing technique is a measure of acetate endogeneous to the sample prior to reaction with vial C and that which was released from acetate esters present in the sample.

The assay is then run on another sample without the use of hydrolysis of vial C. Assuming that the acetate ester comprises ethyl acetate, the acetate that was esterified by ethyl alcohol is calculated by the following technique. The value of acetate ion without the hydrolysis step is subtracted from the value with hydrolysis and is multiplied by 1.45 to express the ester as ethyl acetate. This test is best suited for analyzing liquids containing from 0.5–10 nM of acetate esters.

Other liquids may be assayed for acetate by adjusting the reagent and sample volumes or concentrations. For instance, blood may be assayed after deproteinization by using 0.5–2.0 m of deproteinized sample various concentrations of Reagent A to yield the approximate 3.00 ml volume of Example 1.

What is claimed is:

1. An enzymic assay for acetate ion in a sample fluid comprising the steps of
   a. reacting the acetate ion with adenosine triphosphate in the presence of acetate kinase in an assay fluid to yield acetyl-phosphate and adenosine diphosphate,
   b. reacting the acetyl-phosphate formed in step (a) in said assay fluid with Coenzyme-A in the presence of phosphotransacetylase to form acetyl-Coenzyme A and phosphate, and
   c. assaying the quantity of adenosine diphosphate formed in step (a) by an assay procedure including conversion of said adenosine diphosphate to a different compound in said fluid.

2. The assay of claim 1 in which said sample fluid is of biological orgin.

3. The assay of claim 1 in which said sample fluids is of fruit juice origin.

4. The assay of claim 1 in which said adenosine diphosphate is assayed by the following steps:
   d. reacting said adenosine diphosphate wit phosphoenolpyruvate in the presence of an effective quantity of pyruvate kinase to form adenosine triphosphate and pyruvate,
   e. reacting pyruvate and reduced nicotinamide adenine dinucleotide in the presence of an effective quantity of lactate dehydorgenase to form oxidized nicotinamide adenine dinucleotide, and
   f. detecting the amount of reduced nicotinamide adenine dinucleotide present after the rection of step (e) by the change in optical density of the solution.

5. The method of claim 4 in which the reagents for steps (a), (b) and (c) comprising adenosine triphosphate, Coenzyme A, phosphotransacetylase, acetate kinase, phosphoenol-pyruvate, pyruvate kinase, and reduced nicotaminade adenine dinucleotide are present simultaneously at the commencement of reaction of step (a).

6. The method of claim 5 is which prior to step (a), all of said reagents except for acetate kinase, are premixed and incubated for sufficient time to produce an essentially stable reading by a detector of absorbence in the presence of reactive contaminants in the reagents.

7. The method of claim 6 in which said sample fluid is present during incubation.

8. The assay of claim 1 in which said sample fluid includes an acetate ester to be assayed including the step of:
   d. prior to step (a), hydrolyzing said acetate ester in the presence of an effective quantity of esterase to form acetate ion.

* * * * *